(12) United States Patent
Katsuki et al.

(10) Patent No.: US 8,154,239 B2
(45) Date of Patent: Apr. 10, 2012

(54) MEDICAL MANIPULATOR

(75) Inventors: Ryohei Katsuki, Fujinomiya (JP); Hiroaki Sano, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 386 days.

(21) Appl. No.: 12/570,403

(22) Filed: Sep. 30, 2009

(65) Prior Publication Data

US 2010/0079099 A1 Apr. 1, 2010

(30) Foreign Application Priority Data

Oct. 1, 2008 (JP) .................................. 2008-256171

(51) Int. Cl.
*A61B 17/28* (2006.01)
(52) U.S. Cl. .................................. 318/565; 318/568.11
(58) Field of Classification Search .................. 318/565, 318/568.11, 568.24, 575, 490; 901/2, 9, 901/30, 41; 700/245, 302
See application file for complete search history.

(56) References Cited

U.S. PATENT DOCUMENTS

| | | | |
|---|---|---|---|
| 5,808,665 A * | 9/1998 | Green | 348/65 |
| 6,331,181 B1 | 12/2001 | Tierney et al. | |
| 6,994,716 B2 | 2/2006 | Jinno et al. | |
| 2007/0138992 A1 * | 6/2007 | Prisco et al. | 318/568.21 |
| 2009/0163948 A1 * | 6/2009 | Sunaoshi et al. | 606/205 |

FOREIGN PATENT DOCUMENTS

JP 2004-105451 4/2004

* cited by examiner

*Primary Examiner* — Bentsu Ro
(74) *Attorney, Agent, or Firm* — Oblon, Spivak, McClelland, Maier & Neustadt, L.L.P.

(57) ABSTRACT

A medical manipulator includes an actuator block having a motor, a coupler detachably mounted on the actuator block and having a rotor connected to a rotatable shaft of the motor, a distal-end working unit mounted on a distal end of a joint shaft, which extends from the coupler and is operatively connected to the rotor by a wire, an encoder for detecting an angular displacement of the motor, and a controller for reading a signal from the encoder and comparing the read signal with an operation command value for energizing the motor through a feedback loop. The controller outputs a signal having a level greater than the resolution of the encoder and a lower operation limit of the motor within a range in which the distal-end working unit remains still, and monitors the angular displacement of the motor for thereby determining whether the feedback loop is malfunctioning or not.

6 Claims, 9 Drawing Sheets

MEDICAL MANIPULATOR

CROSS-REFERENCE TO RELATED APPLICATION

This application is based upon and claims the benefit of priority from Patent Application No. 2008-256171 filed on Oct. 1, 2008, in the Japan Patent Office, of which the contents are incorporated herein by reference.

BACKGROUND OF THE INVENTION

1. Field of the Invention

The present invention relates to a medical manipulator for actuating a distal-end working unit on the distal end of a joint shaft with a motor that is energized by a controller, and more particularly to a medical manipulator in which a motor for actuating a distal-end working unit is feedback-controlled based on a comparison of angular displacement of the motor and an operation command value.

2. Description of the Related Art

When performing an endoscopic surgery (also called laparoscopic surgery), it is customary to form a plurality of incisions in the body surface of the patient, insert trocars (tubular instruments) into respective incisions as instrument passage ports, and introduce distal ends of forceps having shafts through the respective trocars into the body cavity to perform a surgical operation on an affected part of the body. Working units such as a gripper for gripping a living tissue, scissors, the blade of an electric scalpel, etc., are mounted on distal ends of the forceps.

An endoscopic surgical operation performed with forceps requires the surgeon to be trained in advance, because the working space in the body cavity is small and the forceps need to be operated using the trocars as fulcrums. Since forceps that have been used heretofore lack joints in the working unit on the distal end thereof, such forceps have a small degree of freedom, and the working unit can be operated only on an extension of the shaft. Therefore, cases that can be handled under the usual training practice for endoscopic surgery are limited to a certain range. The surgeon needs to be trained and highly skilled in order to be able to perform endoscopic surgery on various other cases not within this limited range.

Attempts have heretofore been made to improve conventional forceps and to develop a forceps having a plurality of joints in a working unit thereof (see, for example, Japanese Laid-Open Patent Publication No. 2004-105451). The manipulator disclosed in Japanese Laid-Open Patent Publication No. 2004-105451 comprises a manually operable operating unit, and a working unit replaceably mounted on the operating unit. The disclosed manipulator is free of the limitations and difficulties of conventional forceps, can be operated easily to perform surgical techniques, and can be applied to a wide variety of surgical cases. The manipulator can be used to perform various surgical techniques by replacing the working unit with working units of different types.

The manipulator includes a motor for moving the working unit, and a controller for measuring the angular displacement of the motor with an angle sensor, comparing a signal representative of the measured angular displacement with an operation command value, and controlling the motor through a negative feedback loop based on the result of the comparison. The motor actuates a distal-end working unit mounted on the distal end of a joint shaft through a power transmitting member such as a wire.

A medical robot system has been proposed for actuating such a manipulator via a robot arm (see, for example, U.S. Pat. No. 6,331,181).

In the manipulator described above, the controller compares a signal representative of the measured angular displacement with an operation command value, and controls the motor through a negative feedback loop based on the result of the comparison. The feedback control process makes it possible to operate the distal-end working unit accurately according to the operation command value.

However, if the feedback loop becomes accidentally broken in some way, the feedback control process fails to operate normally. Particularly, if a feedback route from the sensor to a subtracting point is broken, then the feedback loop changes into an open loop, and the controller fails to supply a feedback signal depending on the operation command value, so that the distal-end working unit could possibly operate unexpectedly.

Consequently, the signal line for transmitting the signal from the angle sensor should desirably have a highly reliable construction. The manipulator should also incorporate some means therein for judging whether the feedback system is malfunctioning or not, in preparation for unforeseeable situations. It is desirable that the malfunction judgment be carried out without adversely affecting the surgical operation being performed using the manipulator.

SUMMARY OF THE INVENTION

It is an object of the present invention to provide a medical manipulator, which is capable of judging whether a feedback system is malfunctioning or not without adversely affecting a surgical operation that is being performed using the manipulator.

According to an aspect of the present invention, a medical manipulator comprises an actuator block having a motor including a rotatable shaft, a coupler detachably mounted on the actuator block and having a rotor connected to the rotatable shaft of the motor, a distal-end working unit mounted on a distal end of a joint shaft, which extends from the coupler and is operatively connected to the rotor by a power transmitting member, an angle sensor for detecting an angular displacement of the motor, and a controller for reading a signal from the angle sensor and comparing the read signal with an operation command value for energizing the motor through a feedback loop, wherein the controller temporarily cuts off the feedback loop to turn the feedback loop into an open loop, outputs a current signal to the motor, and monitors the signal from the angle sensor within a range in which the distal-end working unit remains still, for thereby determining whether a system including the motor and the angle sensor is malfunctioning or not.

When the controller outputs a current signal to the motor while the feedback loop is temporarily turned into an open loop, and determines whether the system is malfunctioning or not within a time range in which the distal-end working unit remains still, the medical manipulator does not adversely affect the surgical procedure presently being performed.

The actuator block may include a speed reducer for reducing a speed of rotation of the motor and transmitting the rotation of the motor at the reduced speed to the rotor, and the controller may determine whether the system is malfunctioning or not within a range in which an output shaft of the speed reducer remains still. Since the output shaft of the speed reducer does not move even when the coupler is removed from the actuator block, the operator of the medical manipulator does not sense any visual oddness about the way in which the medical manipulator operates.

The controller may output signals to the motor to rotate the rotational shaft of the motor in respective normal and opposite directions. Since the controller outputs signals to the motor to rotate the rotational shaft thereof in respective normal and opposite directions, even if the motor is less likely to rotate in one of the directions due to gear backlash, the motor is more likely to move in the opposite direction. Accordingly, the motor and the angle sensor respond properly, and the feedback loop can be checked for malfunctioning with increased reliability.

The controller may determine whether the system is malfunctioning or not when the medical manipulator is initialized after the feedback loop is activated, and before the distal-end working unit is operated. Since the feedback loop is judged for malfunctioning when the medical manipulator is initialized, the medical manipulator will be operated with higher reliability during the surgical procedure, in a subsequent operation mode of the medical manipulator.

According to another aspect of the present invention, a medical manipulator comprises an actuator block having a motor including a rotatable shaft, a coupler detachably mounted on the actuator block and having a rotor connected to the rotatable shaft of the motor, a distal-end working unit mounted on a distal end of a joint shaft, which extends from the coupler and is operatively connected to the rotor by a power transmitting member, an angle sensor for detecting an angular displacement of the motor, and a controller for reading a signal from the angle sensor and comparing the read signal with an operation command value for energizing the motor through a feedback loop, wherein the controller monitors the signal from the angle sensor within a range in which the distal-end working unit remains still, by outputting a signal having a level greater than the resolution of the angle sensor and a lower operation limit of the motor, for thereby determining whether a feedback system including the motor and the angle sensor is malfunctioning or not.

When a signal whose level is greater than the resolution of the angle sensor and a lower operation limit of the motor is output to the motor within a range in which the distal-end working unit remains still, only the signal from the angle sensor is changed without moving the distal-end working unit. Consequently, it is possible to determine whether the system is malfunctioning or not, without adversely affecting the surgical procedure being performed.

The above process of the controller can determine whether the system is malfunctioning or not while the feedback loop remains closed.

According to still another aspect of the present invention, a medical manipulator comprises an actuator block having a motor including a rotatable shaft, a coupler detachably mounted on the actuator block and having a rotor connected to the rotatable shaft of the motor, a distal-end working unit mounted on a distal end of a joint shaft, which extends from the coupler and is operatively connected to the rotor by a power transmitting member, an angle sensor for detecting an angular displacement of the motor, a controller for reading a signal from the angle sensor and comparing the read signal with an operation command value for energizing the motor through a feedback loop, and a current sensor for detecting a current value supplied to the motor and supplying the detected current value to the controller, wherein the controller inspects a system including the motor and the angle sensor for malfunctioning, when the signal from the angle sensor remains unchanged and the current value is equal to or greater than a threshold value, depending on an operation at a given time. The above process of the controller can determine whether the system is malfunctioning or not, even in an operation mode of the medical manipulator.

With the medical manipulator according to the present invention, when the controller outputs a current signal to the motor while the feedback loop is temporarily turned into an open loop, and determines whether the system is malfunctioning or not within a time range in which the distal-end working unit remains still, the medical manipulator does not adversely affect the surgical procedure being performed.

Furthermore, when a signal whose level is greater than the resolution of the angle sensor and a lower operation limit of the motor is output to the motor within a range in which the distal-end working unit remains still, only the signal from the angle sensor is changed without moving the distal-end working unit. Consequently, it is possible to determine whether the system is malfunctioning or not without adversely affecting the surgical procedure being performed.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

A medical manipulator according to an embodiment of the present invention will be described below with reference to FIGS. 1 to 9.

Figure 1:
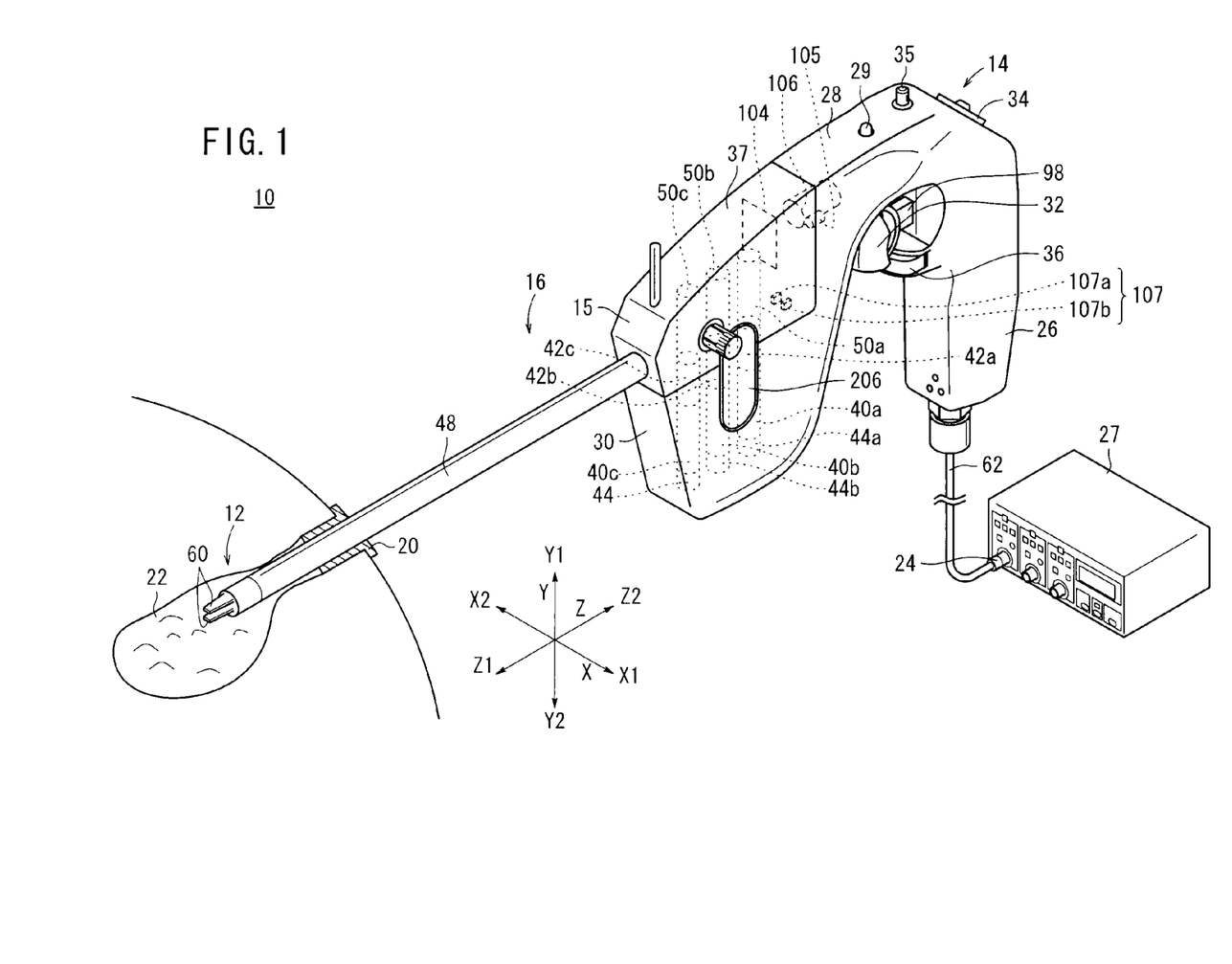
FIG. 1 is a perspective view of a medical manipulator according to an embodiment of the present invention.

As shown in FIG. 1, a medical manipulator 10 according to an embodiment of the present invention includes a distal-end working unit 12 for gripping a portion of a living tissue, a curved needle, or the like in order to carry out a certain surgical treatment. The distal-end working unit 12 typically is referred to as a gripping forceps, a needle driver (needle holder), or the like.

The manipulator 10 comprises an operating unit 14 on a proximal end portion, which is held and operated by a human hand, and a working unit 16 detachably mounted on the operating unit 14. The operating unit 14 is electrically and detachably connected to a controller 27 by a connector 24, thereby making up a manipulator system.

The manipulator 10 basically includes the operating unit 14 and the working unit 16. The controller 27 for electrically controlling the manipulator 10 is connected by the connector 24 to a cable 62, which extends from the lower end of a grip handle 26 of the operating unit 14. Some or all of the functions of the controller 27 may be incorporated into the operating unit 14.

In the following description, the transverse directions in FIG. 1 shall be referred to as X directions, vertical directions as Y directions, and longitudinal directions of a hollow joint shaft 48 as Z directions. Among the X directions, the rightward direction as viewed from the distal end is referred to as an X1 direction, and the leftward direction as an X2 direction. Among the Y directions, the upward direction is referred to as a Y1 direction, and the downward direction as a Y2 direction. Among the Z directions, the forward direction is referred to as a Z1 direction, and the rearward direction as a Z2 direction. Unless otherwise noted, these directions represent directions of the manipulator 10 when the manipulator 10 is in a reference attitude (i.e., neutral attitude). The definitions of the above directions are for illustrative purposes only, and the manipulator 10 can be used in any of various orientations. For example, the manipulator 10 may be used upside down.

The working unit 16 comprises a distal-end working unit 12 for performing a working operation, a coupler 15 connected to an actuator block (actuator) 30 of the operating unit 14, and an elongate hollow joint shaft 48 coupling the distal-end working unit 12 and the coupler 15 to each other. When a predetermined action is performed on the actuator block 30, the working unit 16 can be separated from the operating unit 14, so that the working unit 16 can be cleaned, sterilized, and serviced for maintenance. The actuator block 30 refers to the block on which the working unit 16 is mounted, and is not limited to a structure housing motors (DC motors) 40a, 40b, 40c therein. The actuator block 30 covers a joint surface 30a (see FIG. 3) for connection to a bridge 28.

The distal-end working unit 12 and the joint shaft 48, which are small in diameter, can be inserted into a body cavity 22 through a trocar 20 in the form of a hollow cylinder mounted in an abdominal region or the like of the patient. The distal-end working unit 12 is actuated by the operating unit 14 to perform various surgical techniques, for example, to remove, grip, suture, or ligate (tie-knot) an affected part of the patient's body inside the body cavity 22.

Figure 3:
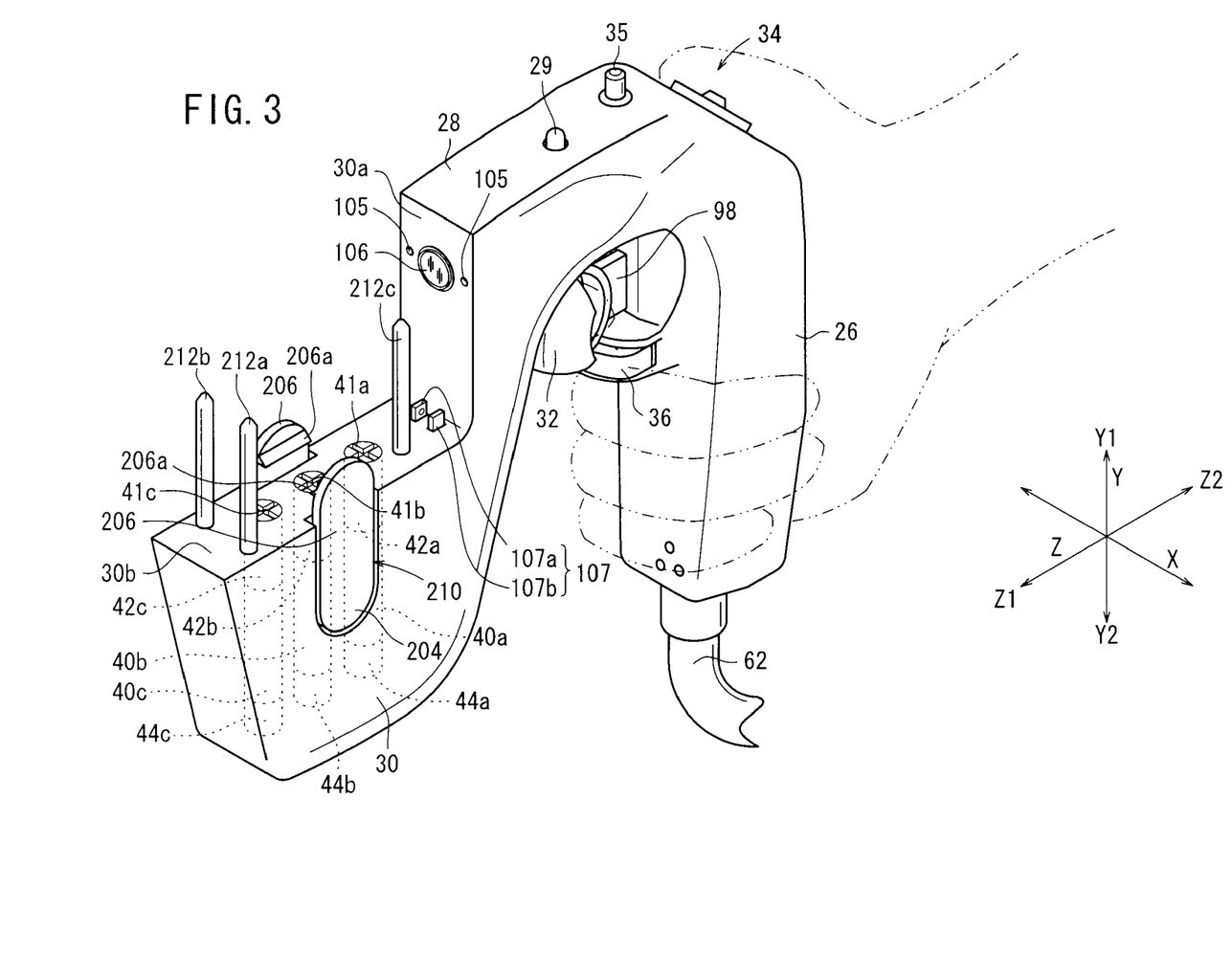
FIG. 3 is a perspective view of the operating unit.

The operating unit 14 includes a grip handle 26 that is gripped by a human hand, the bridge 28 extending from an upper portion of the grip handle 26, and an actuator block 30 connected to a distal end of the bridge 28. As shown in FIG. 3, the grip handle 26 extends in the Y2 direction from the end of the bridge 28, and has a length suitable for being gripped by a human hand. The grip handle 26 has an input means for entering signals for operating the distal-end working unit 12. The input means includes a trigger lever 32 and a switch 36 disposed closely to the grip handle 26 and projecting away from the grip handle 26 in the Z1 direction, and a composite input unit 34 and an operation switch 35, which face away from the grip handle 26 in the Y1 direction.

An LED 29 is mounted on the upper surface of the bridge 28 at a location which can easily be viewed by the operator of the manipulator 10. The LED 29 is spaced from the operation switch 35 in the Z1 direction. The LED 29 serves as an indicator for indicating a controlled state of the manipulator 10. The LED 29 is large enough in size to be easily visually recognizable by the operator, and yet is sufficiently small and light, so as not to interfere with operations of the manipulator 10.

The cable 62 connected to the controller 27 has an end connected to a lower end of the grip handle 26. The grip handle 26 and the cable 62 may be connected to each other by a connector.

The input means, which is incorporated into the operating unit 14 for operating the distal-end working unit 12, will be described below.

The operation switch 35 serves to selectively enable or disable the manipulator 10. The LED 29 is located in a visually recognizable position substantially centrally on the upper surface of the bridge 28, in a juxtaposed relation to the operation switch 35. The LED 29 is turned on in synchronism with the operation switch 35 when the operation switch 35 is turned on. Therefore, when the operator turns on or off the operation switch 35, the operator can reliably recognize and confirm turning on or turning off of the operation switch 35 simply by visually checking the LED 29.

The controller 27 reads the state of the operation switch 35. When the operation switch 35 is turned on, the controller 27 sets the manipulator 10 in an operation mode. When the operation switch 35 is turned off, the controller 27 sets the manipulator 10 in an automatic origin return mode, which returns the motors 40a, 40b, 40c to their origins. After the motors 40a, 40b, 40c have been returned to their origins, the controller 27 sets the manipulator 10 in a stop mode. In the operation mode, the controller 27 enables operation commands to be entered from the operating unit 14 to energize the motors 40a, 40b, 40c. In the stop mode, the controller 27 deenergizes the motors 40a, 40b, 40c regardless of whether operation commands are entered from the operating unit 14 or not. The controller 27 distinguishes such modes, and switches between different energized states of the LED 29 and other lamps based on the distinguished modes.

The composite input unit 34 serves as a composite input means for giving rotational commands, in rolling directions (shaft rotating directions) and yawing directions (left and right directions), to the distal-end working unit 12. The composite input unit 34 includes, for example, a first input means, which operates in shaft rotating directions for giving rotational commands in rolling directions, and a second input means, which operates in left and right directions for giving rotational commands in yawing directions. The trigger lever 32 serves as an input means for giving opening and closing commands to a gripper 60 (see FIGS. 1 and 4) of the distal-end working unit 12.

Figure 2:
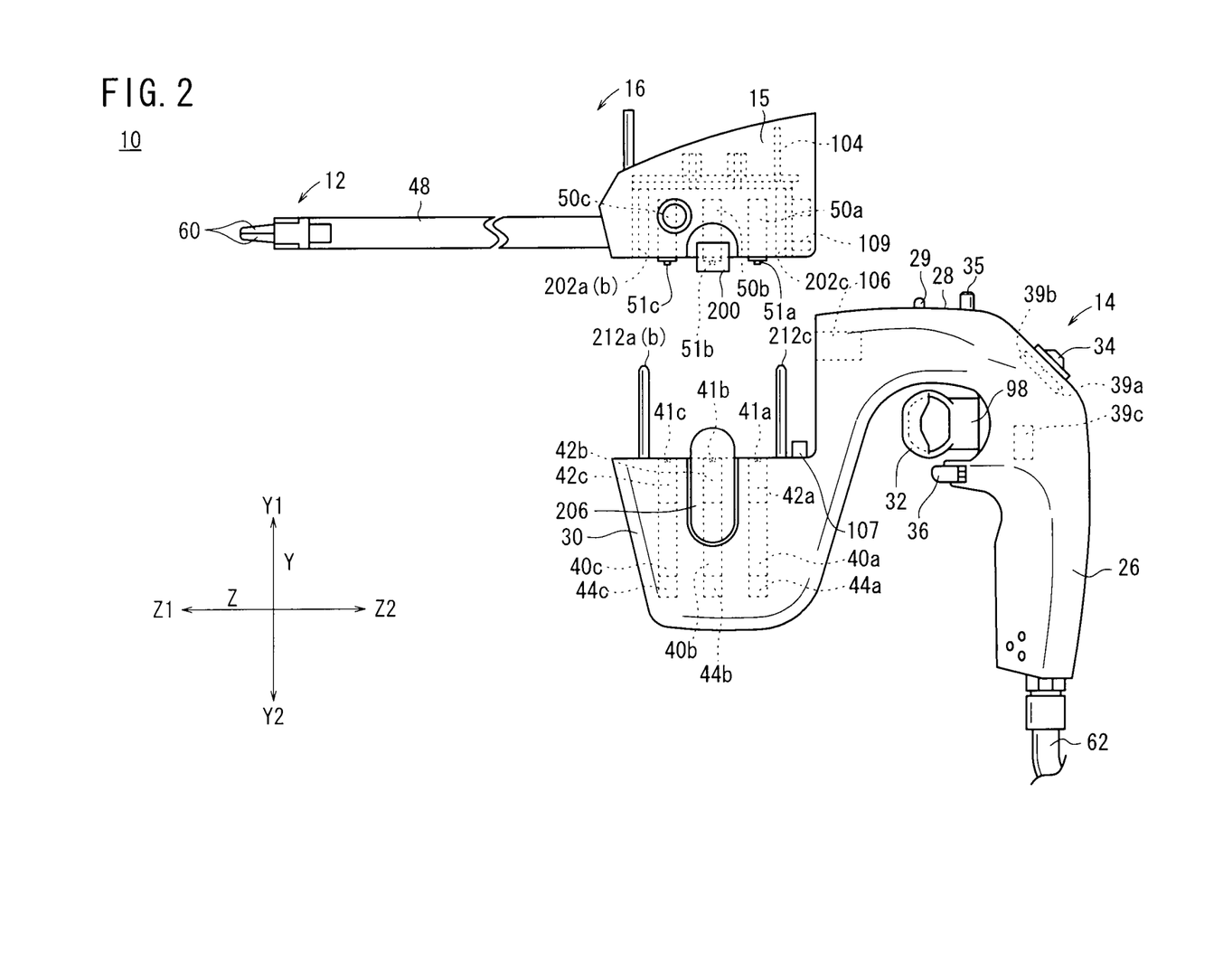
FIG. 2 is a side elevational view of the medical manipulator, with a working unit and an operating unit being separated from each other.

As shown in FIG. 2, the composite input unit 34 and the trigger lever 32 are combined with input sensors 39a, 39b, 39c for detecting movement strokes thereof. The input sensors 39a, 39b, 39c supply detected stroke signals to the controller 27. Based on the supplied stroke signals from the input sensors 39a, 39b, 39c, the controller 27 energizes the motors 40a, 40b, 40c so as to rotate pulleys 50a, 50b, 50c coupled respectively therewith, which in turn actuate respective wires 54a, 54b, 54c (see FIG. 4) that operate the distal-end working unit 12.

As shown in FIGS. 2 and 3, the trigger lever 32 is disposed slightly below the bridge 28 and projects in the Z1 direction. The trigger lever 32 is disposed in a position where it can easily be operated by the index finger of the hand gripping the grip handle 26.

The trigger lever 32 is operatively connected to the grip handle 26 by an arm 98, and is movable toward and away from the grip handle 26. The arm 98 is connected to the input sensor 39c in the grip handle 26. A distance that the trigger lever 32 has moved toward or away from the grip handle 26 is detected by the input sensor 39c, which supplies a signal representing the detected distance to the controller 27. The trigger lever 32 can be pulled by the finger toward the grip handle 26 in the Z2 direction, and can be pushed away from the grip handle 26 by the finger in the Z1 direction. When the trigger lever 32 is thus pulled or pushed, the controller 27 receives a signal from the input sensor 39c and imparts opening and closing commands to the gripper 60.

The switch 36, which is spaced from the trigger lever 32 in the Y2 direction, comprises an alternate switch. When the switch 36 is operated, the gripper 60 remains in a certain state (e.g., a closed state), which is brought about by the trigger lever 32.

As shown in FIGS. 1 and 2, the coupler 15 of the working unit 16 is covered with a resin cover 37. The coupler 15 houses the pulleys 50a, 50b, 50c rotatably therein, which are connected to the respective drive shafts of the motors 40a, 40b, 40c and are rotated thereby. The motors 40a, 40b, 40c are combined with respective speed reducers 42a, 42b, 42c, each in the form of a planetary gear assembly, for example, having a speed reduction ratio ranging from 1:100 to 1:300.

The wires 54a, 54b, 54c (see FIG. 4) are trained respectively around the pulleys 50a, 50b, 50c and extend through a space in the joint shaft 48 to the distal-end working unit 12. The wires 54a, 54b, 54c have portions fixed to the pulleys 50a, 50b, 50c (and also to pulleys 57a, 57b, 57c to be described later) so that the wires 54a, 54b, 54c will not slip on the pulleys 50a, 50b, 50c. The wires 54a, 54b, 54c may be of the same type and have the same diameter.

Figure 4:
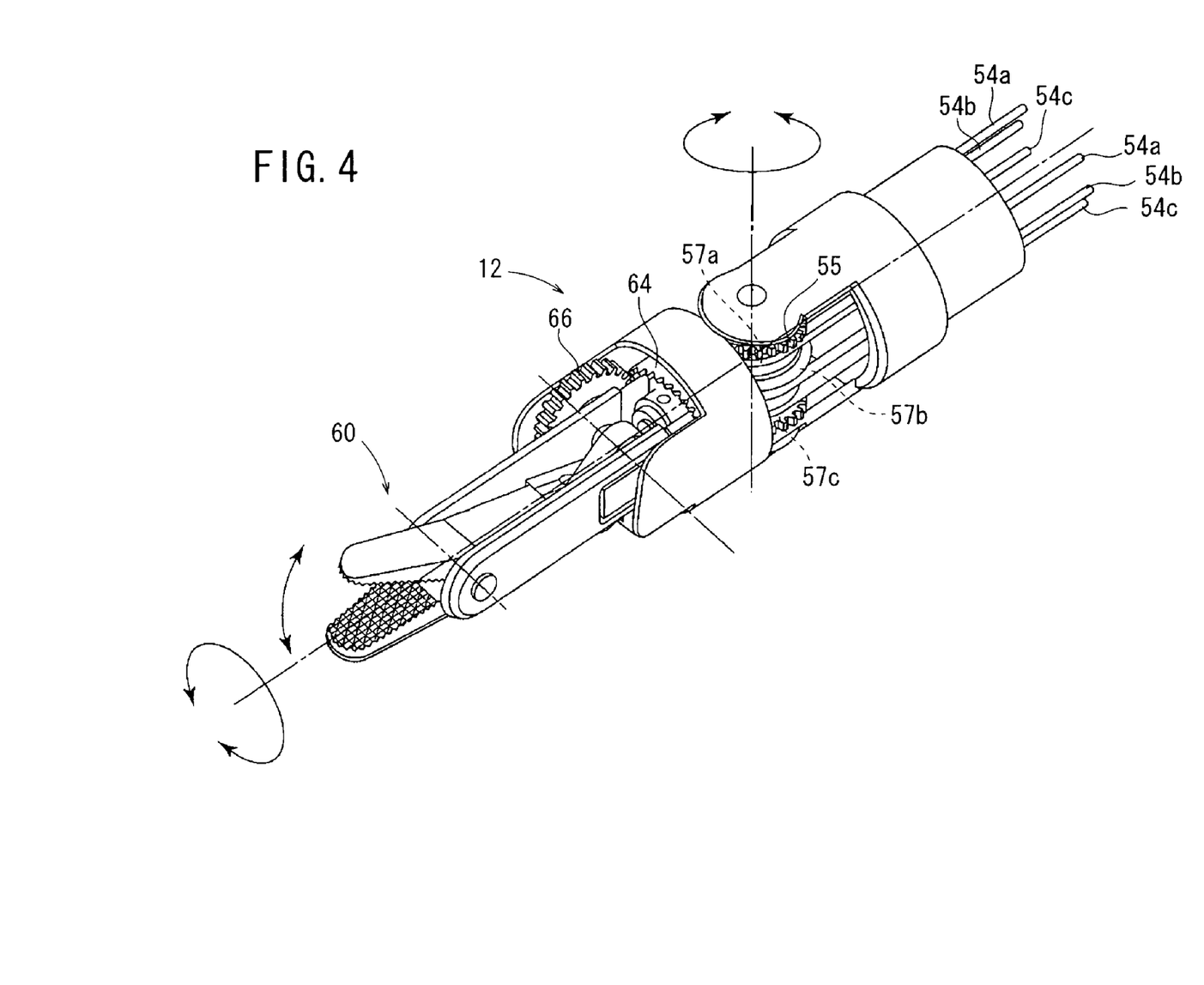
FIG. 4 is a perspective view of a distal-end working unit of the medical manipulator.

As shown in FIG. 4, the wires 54a, 54b, 54c, which extend through the joint shaft 48, are trained respectively around corresponding pulleys 57a, 57b, 57c disposed in the distal-end working unit 12, which includes the gripper 60.

When the pulley 50a is rotated about its own axis by the motor 40a, rotation of the pulley 50a is transmitted through the wire 54a to the pulley 57a, thereby rotating the pulley 57a about its own axis. Rotation of the pulley 57a is then transmitted to a gear 55, a gear ring 64, and a gear 66, which selectively open and close the gripper 60. The pulleys 50a, 50b, 50c, the wires 54a, 54b, 54c, and the pulleys 57a, 57b, 57c jointly make up a power transmitting assembly, which operates mechanisms having three degrees of freedom incorporated in the distal-end working unit 12, for twisting the distal-end working unit 12 in rolling directions, turning the distal-end working unit 12 horizontally in yawing directions, and opening and closing the gripper 60. Since the mechanisms having three degrees of freedom tend to interfere with each other, the motors 40a, 40b, 40c are energized to operate the mechanisms so as not to interfere with each other.

The coupler 15 has two engaging teeth 200 disposed respectively on opposite side surfaces thereof, and three fitting holes 202a, 202b, 202c formed therein, which open on a lower surface thereof. The three fitting holes 202a, 202b, 202c are disposed near ends of the coupler 15 in the Z1 and Z2 directions, and extend in the Y directions.

The actuator block 30 houses therein three motors 40a, 40b, 40c, which extend in parallel to each other, and are arrayed at spaced intervals along the Z directions in association with the respective mechanisms having three degrees of freedom in the distal-end working unit 12. The motors 40a, 40b, 40c are small in size and diameter. The actuator block 30 that houses the motors 40a, 40b, 40c has a flat compact shape. The actuator block 30 is disposed downwardly of the end of the operating unit 14 in the Z1 direction. The motors 40a, 40b, 40c are energized under the control of the controller 27, based on actions made by the operator on the operating unit 14.

The motors 40a, 40b, 40c also are combined with respective rotary encoders (or angle sensors, hereinafter referred to as "encoders") 44a, 44b, 44c for detecting angular displacements of the respective motor drive shafts. The rotary encoders 44a, 44b, 44c supply detected angle signals to the controller 27.

Angular displacements detected by the encoders 44a, 44b, 44c are referred to for causing the three-axis mechanisms of the distal-end working unit 12 to reach desired angles. In order to detect the attitude of the distal-end working unit 12 accurately, the encoders 44a, 44b, 44c may be incorporated into the distal-end working unit 12, for directly detecting angular displacements of the three-axis mechanisms of the distal-end working unit 12 accurately. However, for reasons 1) to 7) to be described in detail below, the encoders 44a, 44b, 44c detect the angular displacements of the motors 40a, 40b, 40c in order to indirectly detect the angular displacements of the three-axis mechanisms.

1) Since the distal-end working unit 12 is small and the space therein is highly limited, it is difficult to incorporate sensors in the distal-end working unit 12. 2) Even if sensors could be incorporated in the distal-end working unit 12, the weight of the manipulator including the distal-end working unit 12 with such sensors incorporated therein would be heavy at the distal end and could not easily be operated. 3) Since the working unit 16 is detachably mounted on the operating unit 14, electric connectors would be needed to provide electric connections for any sensors incorporated in the distal-end working unit 12. 4) The working unit 16 should desirably be free of electric components and electric contact points, because the working unit 16 periodically needs to be cleaned. 5) Depending on the type of working unit 16, high voltage may be applied to the working unit for burning living tissue being treated by the working unit 16, in which case it is difficult to electrically insulate sensors incorporated within the distal-end working unit 12. 6) Since the working unit 16 is expendable, the working unit 16 preferably should be inexpensive. 7) Since the distal-end working unit 12 includes rotatable shafts, and since movable wires 54a, 54b, 54c extend through the joint shaft 48, leads connected to sensors incorporated in the distal-end working unit 12 may become broken, leading to damage to the feedback system including the sensors.

With respect to the above reason 7), inasmuch as the medical manipulator 10 is required to be highly reliable, a negative feedback loop 508 (see FIG. 6) for actuating the distal-end working unit 12 desirably should be constructed from as few units as possible. With the medical manipulator 10, the feedback loop 508 comprises only the operating unit 14, the cable 62, and the controller 27, and hence the medical manipulator 10 is highly reliable.

As shown in FIG. 2, the pulleys 50a, 50b, 50c in the coupler 15 have respective criss-cross coupling teeth 51a, 51b, 51c on lower ends thereof in the Y2 direction, and the rotatable shafts of the motors 40a, 40b, 40c in the actuator block 30 have respective criss-cross coupling recesses 41a, 41b, 41c. The coupling teeth 51a, 51b, 51c can engage in the respective coupling recesses 41a, 41b, 41c. When the coupler 15 is mounted on the actuator block 30, the coupling teeth 51a, 51b, 51c engage in the respective coupling recesses 41a, 41b, 41c in order to transmit the rotation of the motors 40a, 40b, 40c to the pulleys 50a, 50b, 50c. The coupling teeth 51a, 51b, 51c and the coupling recesses 41a, 41b, 41c may have shapes other than criss-cross shapes.

An ID unit 104, which carries an ID (identification) mark for identifying the individual working unit 16, is disposed on the coupler 15.

The ID mark carried by the ID unit 104 comprises a QR code in the form of a two-dimensional bar code for identifying the working unit 16. The QR code is peculiar to a single working unit 16, and hence different QR codes are assigned respectively to different working units 16. The QR code contains various pieces of information including the type, specifications, serial number, production factory, production date, tradename, etc., of the working unit 16.

The operating unit 14 includes a camera 106 for reading the QR code of the ID unit 104 of the connected working unit 16, and for supplying the read QR code to the controller 27. The camera 106 is disposed in a position facing the ID unit 104. The operating unit 14 also includes two LEDs 105, which are positioned one on each side of the camera 106, for illuminating the ID unit 104 of the connected working unit 16. The camera 106 may be replaced with a bar-code reader or a bar-code scanner for reading the ID mark of the ID unit 104.

In order to remove the coupler 15 from the operating unit 14, the operator simultaneously presses levers 206 disposed on respective opposite sides of the actuator block 30, thereby tilting the levers 206 outwardly to bring tapered wedges 206a of the levers 206 out of engagement with respect to engaging teeth 200 disposed on respective opposite sides of the coupler 15. Thereafter, the coupler 15 can be pulled and removed from the operating unit 14 upwardly in the Y1 direction. The actuator block 30 has three alignment pins 212a, 212b, 212c on an upper surface thereof. The alignment pins 212a, 212b, 212c can be fitted respectively into fitting holes 202a, 202b, 202c formed in the coupler 15, for thereby stably holding the coupler 15 on the actuator block 30. In order to connect the coupler 15 to the operating unit 14, the operator aligns the alignment pins 212a, 212b, 212c respectively with the fitting holes 202a, 202b, 202c, and inserts the alignment pins 212a, 212b, 212c respectively into the fitting holes 202a, 202b, 202c by lowering the coupler 15 in the Y2 direction. The levers 206 are displaced outwardly while sliding over the outer surfaces of the engaging teeth 200. Then, the levers 206 snap back under the resiliency of the resilient members, thus bringing the wedges 206a into engagement with the engaging teeth 200, whereby the coupler 15 becomes mounted completely on the actuator block 30.

A working unit detecting means 107 for detecting whether the coupler 15 has been placed on the actuator block 30 or not is disposed on an upper surface 30b of the actuator block 30 at one end thereof in the Z2 direction. The working unit detecting means 107 is in the form of a photointerruptor comprising an LED 107a as a light emitter and a photodiode 107b as a light detector, which are positioned in confronting relation to each other. When a light shield 109 (see FIG. 2) on the rear end of the coupler 15 is inserted between the LED 107a and the photodiode 107b, the light shield 109 blocks light emitted from the LED 107a toward the photodiode 107b, thereby detecting that the coupler 15 is mounted on the actuator block 30. The LED 107a and the photodiode 107b confront each other in the X directions, and are disposed closely to each other.

The actuator block 30 includes a pair of independent engaging fingers 210 for holding the coupler 15 of the working unit 16 and the three alignment pins 212a, 212b, 212c for positioning and holding the coupler 15.

The two engaging fingers 210 are pivotally mounted in symmetrical positions on respective outer side surfaces thereof, which face in the X1 and X2 directions. The engaging fingers 210 comprise respective pusher surfaces 204 and respective levers 206, which extend in the Y1 direction from the pusher surfaces 204. The levers 206 project slightly from the upper surface of the actuator block 30 in the Y1 direction, and have respective tapered wedges 206a on upper inner surfaces thereof for engaging with the respective engaging teeth 200 on outer side surfaces of the coupler 15 when the coupler 15 is mounted on the actuator block 30. The engaging fingers 210 are normally biased by resilient members, not shown, to displace the levers 206 inwardly toward each other.

The alignment pins 212a, 212b, 212c are disposed for alignment with the respective fitting holes 202a, 202b, 202c. Among the three alignment pins 212a, 212b, 212c, two of the alignment pins 212a, 212b are disposed near the end of the upper surface of the actuator block 30 in the Z1 direction, whereas the other alignment pin 212c is disposed near the other end of the upper surface of the actuator block 30 in the Z2 direction. The alignment pins 212a, 212b, 212c extend in the Y1 direction. Alignment pins 212a and 212b, which are disposed near the end of the upper surface of the actuator block 30 in the Z1 direction, are spaced from each other in the X directions.

Since the actuator block 30 has three alignment pins 212a, 212b, 212c, the coupler 15 is supported by the actuator block 30 at three positions corresponding to the alignment pins 212a, 212b, 212c, whereby the coupler 15 is simply and reliably positioned with respect to the actuator block 30. Since the three alignment pins 212a, 212b, 212c are not positioned in a linear manner, but rather in a triangular pattern, the alignment pins 212a, 212b, 212c can hold the coupler 15 stably against twisting forces applied in any direction. At least two of the alignment pins 212a, 212b, 212c may be effective to reliably position and hold the coupler 15 stably on the actuator block 30. If two such alignment pins are spaced from each other in the Z directions, then the alignment pins are effective to hold the coupler 15 more stably on the actuator block 30.

A communication system 700 involving the controller 27 and the operating unit 14 will be described below with reference to FIG. 5.

The communication system 700 comprises the controller 27, the operating unit 14, the connector 24, and the cable 62.

The controller 27 includes a CPU 600 connected to an FPGA (Field Programmable Gate Array) 602 and a motor driver 606. The FPGA 602 comprises an interface 604 and a counter 603.

The operating unit 14 includes an A/D converter (ADC) 618.

Figure 5:
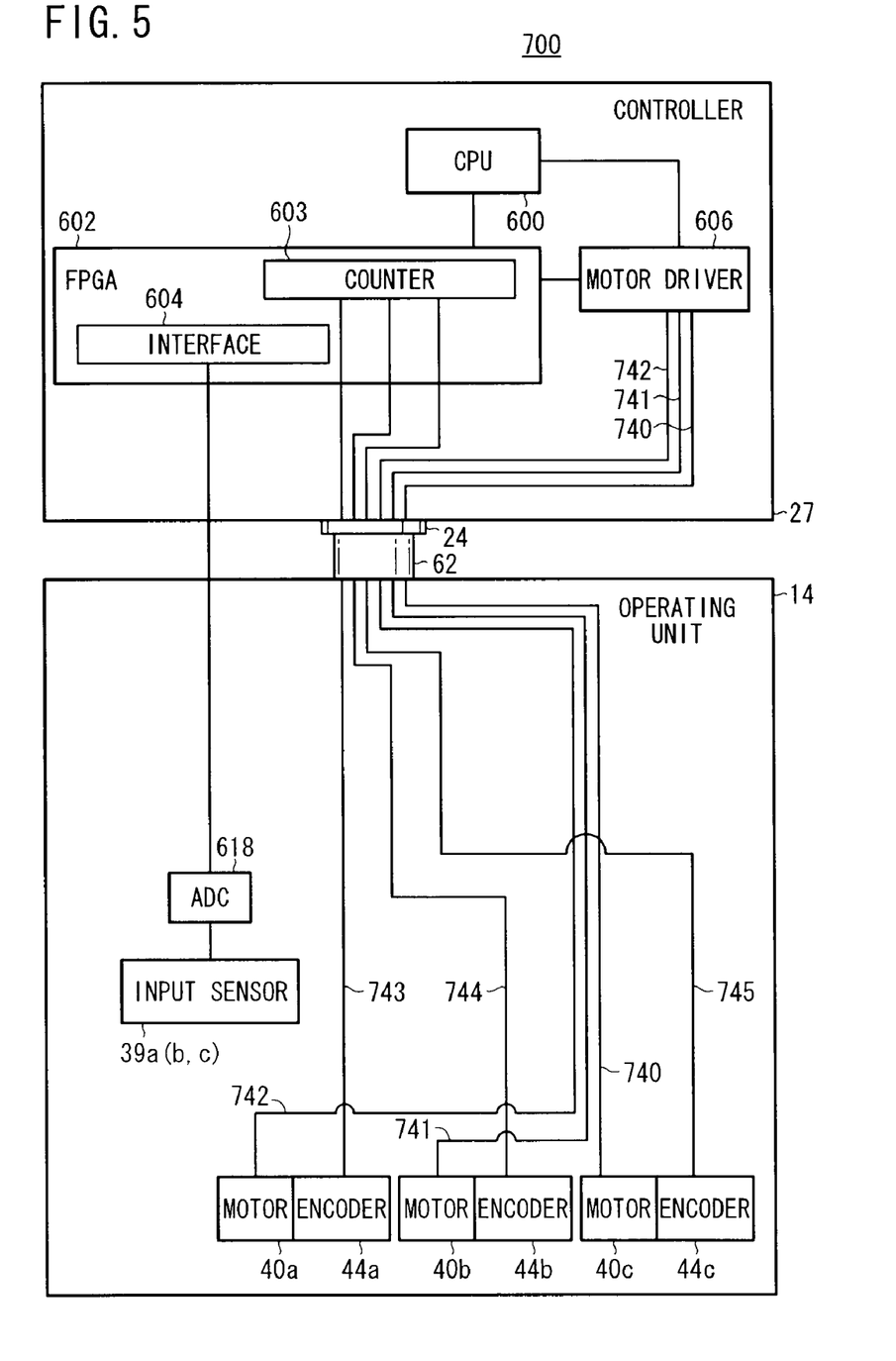
FIG. 5 is a block diagram of a controller and the operating unit, which are connected to each other by a cable.

The communication system 700 also transmits signals to and from the camera 106, the LED 29, the LED 107a, the switch 36, and the photodiode 107b, which are omitted from illustration in FIG. 5. Since the signals from the camera 106 represent a large amount of image information, such signals may be transmitted by an independent signal transmitting means if necessary.

Power lines 740, 741, 742, each comprising two leads, which are connected respectively to the motors 40a, 40b, 40c, extend through the cable 62 to the motor driver 606 of the controller 27. Signal lines 743, 744, 745, each of which comprises two leads for sending respective phase output pulse signals, i.e., A-phase and B-phase signals that are 90° out of phase with each other, are connected respectively to the encoders 44a, 44b, 44c, and extend through the cable 62 to the counter 603. The counter 603 counts pulses based on the A-phase and B-phase signals from the encoders 44a, 44b, 44c, determines the angular displacements of the motors 40a, 40b, 40c, and supplies the determined angular displacements to the CPU 600. Analog signals output from the input sensors 39a, 39b, 39c are supplied through the A/D converter 618 to the interface 604.

The output signals from the encoders 44a, 44b, 44c may be multiplied by a multiplier for increasing detection accuracy, sometime before the output signals are supplied to the counter 603, or processed and supplied as angular displacement signals to the CPU 600. The communication system 700 has a communication rate, which is high enough so as not to adversely affect the feedback control process performed through the feedback loop 508 (see FIG. 6).

A system of the medical manipulator 10 for judging whether the feedback loop 508 is malfunctioning or not will be described below with reference to FIG. 6. Although the distal-end working unit 12 of the medical manipulator 10 includes mechanisms having three degrees of freedom, the system shown in FIG. 6 schematically illustrates only the mechanism thereof involving the yaw axis.

Figure 6:
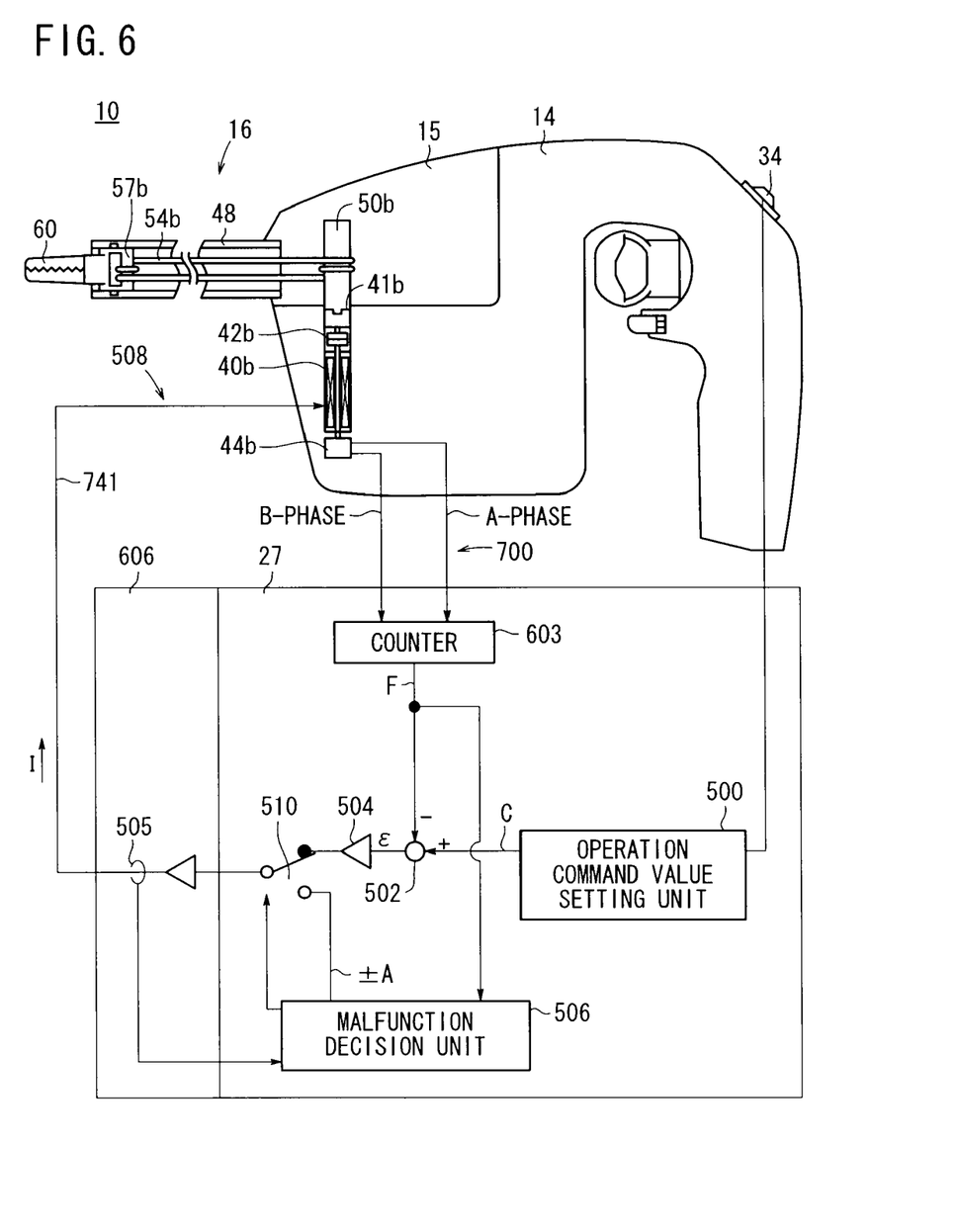
FIG. 6 is a schematic view showing a system of the medical manipulator for judging whether a feedback loop thereof is malfunctioning or not.

As shown in FIG. 6, the controller 27 comprises an operation command value setting unit 500 for determining a target angular displacement in the yawing direction based on a signal obtained from the composite input unit 34 and outputting the determined target angular displacement as an operation command value C, a subtracting point 502 for determining the error or difference E between the angular displacement F of the motor 40b supplied from the counter 603 and the operation command value C, a compensator 504 for compensating for the error $\epsilon$, and a malfunction decision unit 506 for determining whether the feedback loop 508 is malfunctioning or not based on the operation command value C and the angular displacement F. The controller 27 also includes an opener for temporarily cutting off the path between the counter 603 and the subtracting point 502 to thereby turn the feedback loop 508 into an open loop, and an input switcher 510 for selecting either one of the operation command value setting unit 500 and the malfunction decision unit 506 as an input source thereof. The input switcher 510 has an output terminal connected to a current sensor 505, which comprises a Hall device, for example. The opener and the input switcher 510 are operated by the malfunction decision unit 506. When the medical manipulator 10 is in a normal operation mode, the opener connects the path between the counter 603 and the subtracting point 502, thereby closing the feedback loop 508, and the input switcher 510 selects the operation command value setting unit 500 as its input source.

The operation command value setting unit 500 integrates positive and negative signals obtained from the composite input unit 34 into the operation command value C. The operation command value setting unit 500 may set an appropriate dead zone for the positive and negative signals obtained from the composite input unit 34, so that the operation command value C will not fluctuate when the medical manipulator 10 is not in operation. The compensator 504 serves as a control means for compensating for the error $\epsilon$ to converge to zero (0) quickly and stably. The compensator 504 performs a PID compensating process, for example.

When the medical manipulator 10 is in a check mode, at a time when the medical manipulator 10 is initialized but before the distal-end working unit 12 is operated, the malfunction decision unit 506 controls the opener to cut off the path between the counter 603 and the subtracting point 502 to thereby turn the feedback loop 508 into an open loop, and also controls the input switcher 510 to select the malfunction decision unit 506 as its input source. In the check mode, the malfunction decision unit 506 supplies small inspection signals $\pm A$ to the input switcher 510 and monitors the angular displacement F of the motor 40b supplied from the counter 603 to determine whether the feedback loop 508, which includes the motor 40b and the encoder 44b, is malfunctioning or not.

The malfunction decision unit 506 can also determine whether the feedback loop 508 is malfunctioning or not in a composite fashion, based on a current value I detected by the current sensor 505.

When the malfunction decision unit 506 detects a malfunction, the controller 27 displays a malfunction indication and deenergizes the motor driver 606. Some or all of the functions of the controller 27 shown in FIG. 6 may be implemented by software.

The angular displacement F of the motor 40b is produced when the A-phase and B-phase signals output from the encoder 44b are supplied to the counter 603, and pulses of the A-phase and B-phase signals are counted by the counter 603. The error $\epsilon$ produced by the subtracting point 502 is compensated for by the compensator 504. The motor driver 606 outputs a current to energize the motor 40b, which in turn rotates the drive shaft of the motor 40b. The rotational speed of the drive shaft of the motor 40b is reduced by the speed reducer 42b, which transmits a reduced-speed rotation from the output shaft thereof to the pulley 50b. The pulley 50b moves the wire 54b to rotate the pulley 57b, which operates the distal-end working unit 12 in the yawing directions. While the distal-end working unit 12 is in operation, the encoder 44b outputs A-phase and B-phase signals depending on the direction and the amount by which the motor 40b has rotated. The counter 603 counts the pulses of the A-phase and B-phase signals, and outputs the angular displacement F of the motor 40b. When the distal-end working unit 12 reaches the target angular displacement, the operation command value C and the angular displacement F are equal to each other, while the error $\epsilon$ is represented by $\epsilon = C - F = 0$. Therefore, the current output from the motor driver 606 becomes nil, thus stopping the motor 40b, the pulley 50b, and the pulley 57b. The negative feedback loop 508 is made up collectively by the motor 40b which serves as an actuator, the encoder 44b acting as a sensor, and the subtracting point 502, etc., of the medical manipulator 10.

Sequences for detecting malfunction of the feedback loop 508 of the medical manipulator 10 will be described below. The malfunction detecting sequences include a sequence performed in the check mode at a time when the medical manipulator 10 is initialized after the feedback loop 108 has been activated but before the distal-end working unit 12 is operated, and a sequence performed in the operation mode, in which inputs from the composite input unit 34 and the trigger lever 32 are validated while the distal-end working unit 12 is in operation.

Figure 7:
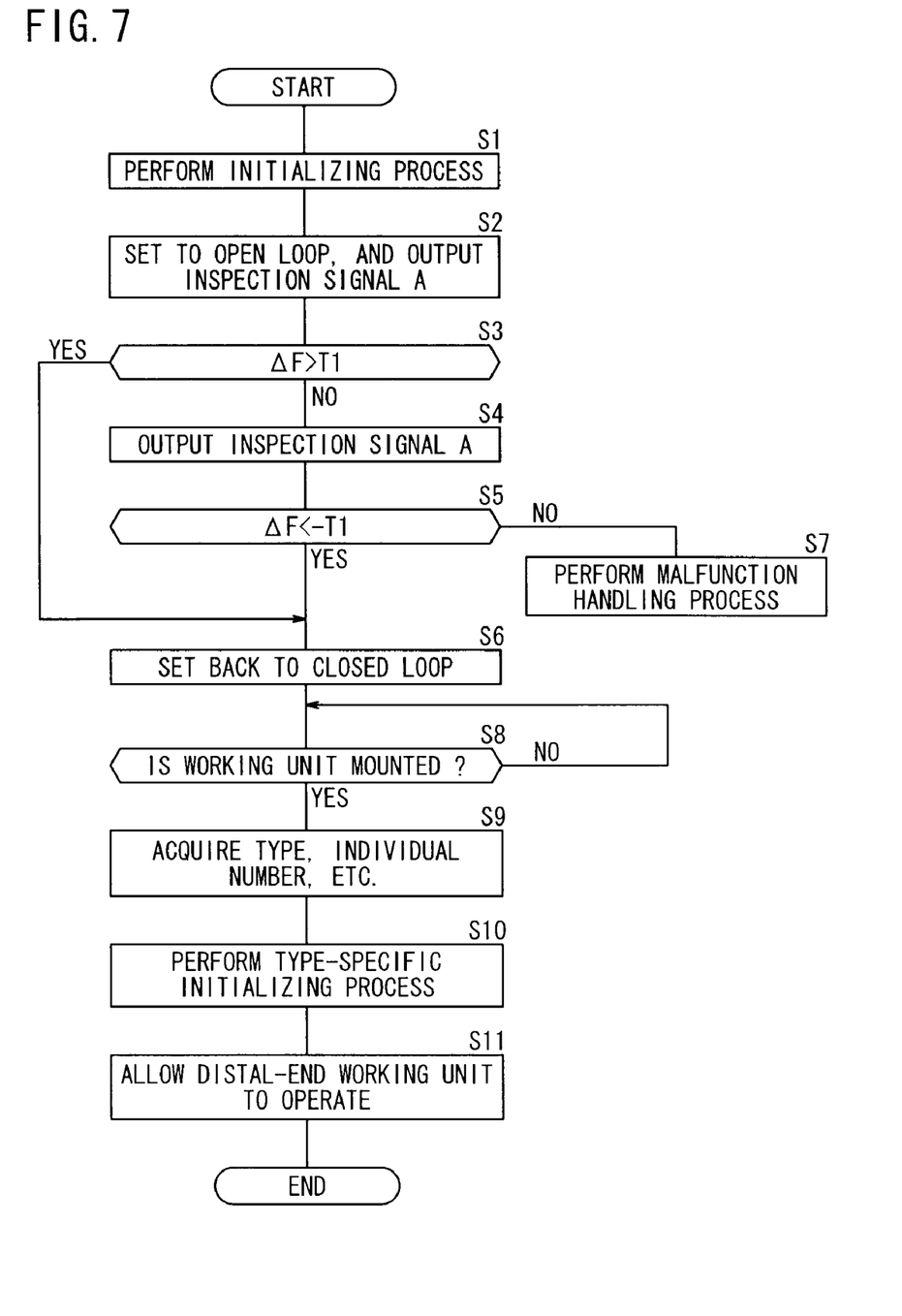
FIG. 7 is a flowchart of a sequence for judging whether the feedback loop is malfunctioning or not in a check mode after the feedback loop has been activated, and for transitioning to an operation mode following the check mode.

First, the sequence for detecting a malfunction of the feedback loop 508 in the check mode after the feedback loop 108 has been activated will be described below with reference to FIG. 7. The check mode shown in FIG. 7 is carried out immediately after the feedback loop 108 has been activated.

In step S1, the medical manipulator 10 is initialized. Specifically, the count value of the counter 603 and the operation command value C are preset to zero (0), and any inputs from the composite input unit 34 and the trigger lever 32 are temporarily made invalid. It is confirmed that the angular displacement F obtained through the communication system 700 is nil. At this time, it is assumed that the working unit 16 is mounted on the operating unit 14.

In step S2, the opener cuts off the path between the counter 603 and the subtracting point 502 to thereby turn the feedback loop 508 into an open loop, and the input switcher 510 selects the malfunction decision unit 506 as its input source. The malfunction decision unit 506 supplies a small inspection signal A to the input switcher 510 and monitors the angular displacement F of the motor 40b, which is output from the counter 603. At this time, the malfunction decision unit 506 may refer to the current sensor 505 in order to check if a current I depending on the inspection signal A is generated normally or not, and may provide a suitable current feedback.

The inspection signal A is a small signal, and the motor torque produced by the current I depending on the inspection signal A is small, so that the current I essentially will not actuate the speed reducer 42b or the distal-end working unit 12. However, the produced motor torque can actuate the speed reducer 42b and the distal-end working unit 12 within a certain non-load range, which is commensurate with the play and backlash of the gears of the speed reducer 42b and the distal-end working unit 12. Although the non-load range is considerably small, it can be detected by the encoder 44b. At this time, movement of the distal-end working unit 12 cannot be confirmed at least with normal perception, and such movement does not make the operator feel visually odd about the way in which the medical manipulator 10 operates. The inspection signal ±A can be determined by computation, simulation, experimentation, or the like.

If the feedback loop 508 is not malfunctioning, then the motor 40b rotates within the non-load range, and the rotation of the motor 40b is detected by the encoder 44b. Thus, the operator can recognize that the feedback loop 508 is operating normally.

If a drive line of the feedback loop 508, i.e., the power line 741, is suffering from a malfunction such as a disconnection, short circuit, or the like, then the motor 40b is not rotated, or is rotated only slightly. If a feedback line of the feedback loop 508, i.e., the encoder 44b, the counter 603, the communication system 700, and interconnections therebetween, is suffering from a malfunction, then no rotation of the motor 40b is detected, and the angular displacement F supplied to the subtracting point 502 remains nil. Irrespective of whether the drive line or the feedback line of the feedback loop 508 is suffering from a malfunction, therefore, the angular displacement F remains unchanged.

In step S3, a change ΔF in the angular displacement F and a threshold value T1 are compared with each other to confirm that ΔF>T1. The threshold value T1 is a small value for excluding measurement errors. If ΔF=T1, i.e., if the angular displacement F undergoes no substantial change, then the motor 40b may not be rotating due to a malfunction of the drive system for the motor 40b, e.g., the motor driver 606. Control then goes to step S4 for a more detailed check. If ΔF>T1, then since the feedback loop 508 is functioning normally, the input switcher 510 selects the operation command value setting unit 500 as its input source, and the feedback loop 508 is closed in step S6. At this time, the check mode shown in FIG. 7 is finished. Then, control proceeds to the operation mode shown in FIG. 8.

There are possibly three cases which can lead to ΔF being less than or equal to T1 (ΔF=T1). The first case is when no current is supplied from the power line 741 and the motor 40b is not energized. The second case occurs when, although the motor 40b is energized, the feedback line of the feedback loop 508 suffers from a malfunction and the angular displacement F of the motor 40b is not detected. The third case occurs when, although the feedback loop 508 is normal, the motor 40b is less likely to move in a normal direction depending on the polarity of the gear backlash. In the third case, the motor 40b is more likely to move in an opposite direction, but is mechanically less likely to move in a normal direction. Since the inspection signal A is small, the torque generated by the motor 40b is not large enough in the third case. In the third case, the motor 40b will still be properly energized in a subsequent operation mode.

In step S4, the inspection signal A is changed to an inspection signal −A.

In step S5, the change ΔF in the angular displacement F and the threshold value T1 are compared with each other to confirm that ΔF<−T1. If ΔF=−T1, then it is judged that the feedback loop 508 is suffering from a malfunction. If ΔF<−T1, then the feedback loop 508 is operating normally. This corresponds to the third case, in which the motor 40b is mechanically less likely to move in a normal direction due to gear backlash, but is more likely to move in the opposite direction. The feedback loop 508 is judged at least to be electrically normal. Control then proceeds to step S6, whereupon the check mode is finished.

If ΔF=−T1, then it is judged that the feedback loop 508 is suffering from a malfunction in the first case or the second case. Control then proceeds to step S7 to carry out a malfunction handling process. In the malfunction handling process, the current I is brought back to zero (0), a predetermined malfunction alarm is generated, and the motor driver 606 is deenergized.

According to the sequence for determining whether the feedback loop 508 is malfunctioning or not, in the check mode, as described above, the feedback loop 508 is temporarily changed into an open loop, and the inspection signal ±A is output to the motor 40b to cause the motor 40b to produce a torque, which is small enough to keep the distal-end working unit 12 from moving. The motor 40b is then rotated in a non-load range because of gear backlash, and the signal from the encoder 44b is changed without moving the distal-end working unit 12. Therefore, the operator is able to judge whether a malfunction in the feedback loop 508 has occurred, without sensing any visual oddness about the way in which the medical manipulator 10 operates. Since the feedback loop 508 includes the communication system 700, the communicating function of the communication system 700 also is checked.

Furthermore, inasmuch as the motor 40b is energized only to an extent in which the distal-end working unit 12 is not moved, the feedback loop 508 can be checked for malfunctioning, even when the distal-end working unit 12 has reached the end of its operating range, e.g., when the gripper 60 is closed.

Moreover, the motor 40b is energized by the inspection signals ±A for rotation in both normal and opposite directions. Therefore, even if the motor 40b is less likely to rotate in one of the directions due to gear backlash, the motor 40b is more likely to rotate in the other direction. Consequently, the motor 40b and the encoder 44b respond properly, and the feedback loop 508 can be checked for malfunctioning with increased reliability.

Since the feedback loop 508 is judged for malfunctioning in the check mode when the medical manipulator 10 is initialized, the medical manipulator 10 can be operated with higher reliability when a surgical procedure is carried out in a subsequent operation mode.

The encoder 44b is used as an angle sensor, and outputs A-phase and B-phase pulse signals. Since the controller 27 checks the feedback loop 508 based on the count value of the counter 603, which counts the pulses of the A-phase and B-phase pulse signals, the controller 27 can simply and reliably determine whether the feedback loop 508 is malfunctioning or not.

Since the current I corresponding to the inspection signals ±A is small, no wasteful energy will be consumed for energizing the motor 40b.

Although, in the sequence shown in FIG. 7, it has been assumed that the working unit 16 is mounted on the operating unit 14, the working unit 16 may not actually be mounted on the operating unit 14 in all cases. If the working unit 16 is not mounted on the operating unit 14, then the inspection signals ±A may be of a magnitude so as to energize the motor 40b in a non-load range, corresponding to the backlash of the gears of the speed reducer 42b. Assuming that the inspection signals ±A have such a magnitude, even when the coupler 15 is removed from the actuator block 30, the operator does not experience any sense of visual oddness, because the exposed output shaft of the speed reducer 42b does not move.

While the feedback loop 508 remains closed, a positional signal, whose level is greater than the resolution of the encoder 44b and the lower operation limit of the motor 40b, but whose level is not strong enough to move the distal-end working unit 12, may be output as an operation command value C to the motor 40b. The signal from the encoder 44b may be monitored to determine whether the feedback loop 508 is malfunctioning or not. According to this alternative process, it is possible to determine whether the feedback loop 508 is malfunctioning or not while the feedback loop 508 remains closed.

In step S8, the controller 27 confirms the signal from the working unit detecting means 107, and waits until the working unit 16 is mounted on the operating unit 14. Once the controller 27 confirms that the working unit 16 has been mounted on the operating unit 14, control proceeds to step S9.

In step S9, the camera 106 captures an image of the ID unit 104, and the controller 27 acquires the type, individual number, etc., of the working unit 16.

In step S10, the controller 27 performs a type-specific initializing process based on the type of working unit 16.

In step S11, the controller 27 validates inputs from the composite input unit 34 and the trigger lever 32, and also validates the operation command value setting unit 500, thereby allowing the distal-end working unit 12 to operate based on actions of the operator. Thereafter, the operation command value setting unit 500 outputs an operation command value C to actuate the distal-end working unit 12, in all but certain exceptional processing modes including a stop mode, an origin return mode, etc.

The sequence for detecting a malfunction of the feedback loop 508 in the operation mode will be described below with reference to FIG. 8. The sequence shown in FIG. 8 is carried out at given small time intervals during the operation mode.

Figure 8:
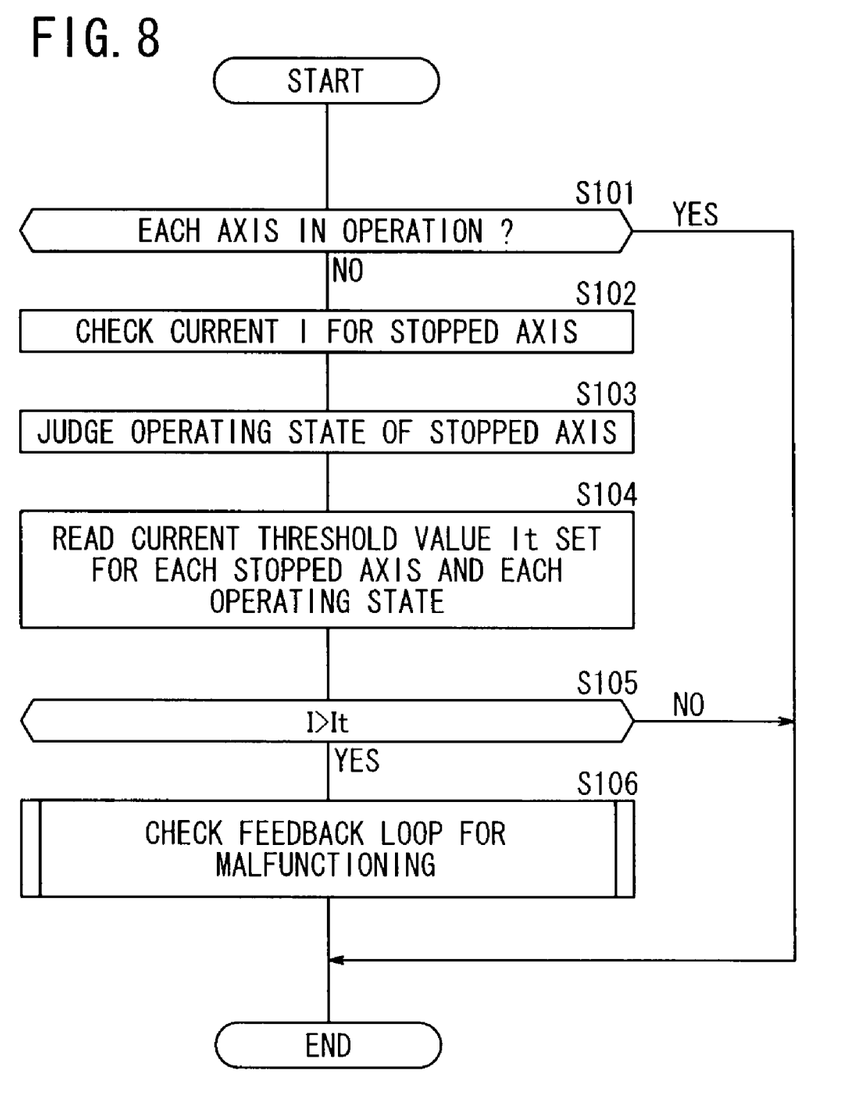
FIG. 8 is a flowchart of a sequence for judging whether the feedback system is malfunctioning or not in the operation mode.

In step S101 shown in FIG. 8, the malfunction decision unit 506 refers to the angular displacement F in order to determine whether each of the axes of the distal-end working unit 12 is in operation or not. Basically, the malfunction decision unit 506 waits, even if only one of the three axes of the distal-end working unit 12 is in operation. However, the malfunction decision unit 506 may still perform the determining sequence, described below, even if one of the three axes of the distal-end working unit 12 is stopped.

In step S102, the malfunction decision unit 506 refers to the current sensor 505, to check the current I for the stopped axis.

In step S103, the malfunction decision unit 506 determines the operating state of the stopped axis, according to a given operating state determining process. The operating state determining process determines the operating state of the gripper 60, for example, as one of four operating states, i.e., an operating state in which the gripper 60 is stopped under no load, an operating state in which the gripper 60 is gripping a workpiece, e.g., a needle, an operating state during which the gripper 60 is being opened, and an operating state during which the gripper 60 is being closed. The gripper 60, which is stopped while being opened and closed in the latter two operating states, may possibly be malfunctioning. The gripper 60, which is stopped while gripping a workpiece in the former two operating states, may also possibly be malfunctioning depending on the current I that is output from the motor driver 606.

In step S104, the malfunction decision unit 506 reads a current threshold value It, which is set for each of the operating states determined in step S103, from a given memory for each stopped axis.

In step S105, the malfunction decision unit 506 compares the current I with the current threshold value It. If I>It, then control goes to step S106. If I=It, then the present cycle of the sequence is ended.

In step S106, the malfunction decision unit 506 checks the feedback loop 508 for malfunctioning, since the feedback loop 508 is highly likely to be malfunctioning because the current I, which is greater than the current threshold value It, is flowing through the stopped axis. Specifically, when the flowing current I is greater than the current threshold value It, the motor corresponding to the stopped axis is considered to be generating a torque. However, since the angular displacement F is not changed, the mechanical components involved may be mechanically stopped, or the feedback loop 508 including the corresponding encoder, the counter 603, etc., may be malfunctioning. Therefore, an inspecting process, which is the same as steps S2 to S7 shown in FIG. 6, is carried out in order to inspect the feedback loop 508. When the gripper 60 is gripping the workpiece while it is stopped, a considerably large current is supplied to the motor to generate the gripping force. Therefore, the current threshold value is read for each axis and for each operating state.

According to the sequence shown in FIG. 8, when the distal-end working unit 12 is stopped, i.e., when the angular displacement F is not changed, and also when the current I that is flowing is equal to or greater than the current threshold value It depending on the operation being conducted at that time, the feedback loop 508 is inspected for malfunctioning. Therefore, the feedback loop 508 can be determined for malfunctioning in the normal operation mode, whereby reliability of the medical manipulator 10 is increased.

The system shown in FIG. 6, and the sequences shown in FIGS. 7 and 8, schematically illustrate only the mechanism involving the yaw axis. However, feedback loops for controlling other mechanisms involving the roll axis and the gripper 60 can similarly be provided to determine whether such mechanisms are malfunctioning or not, in the same manner as described above. The feedback loops for controlling mechanisms involving the yaw axis and the roll axis and the gripper 60 may simultaneously be provided to determine whether these mechanisms are malfunctioning. When a malfunction in any of the feedback loops for controlling mechanisms involving the yaw axis, the roll axis and the gripper 60 is detected, a warning may be issued in order for the operator to recognize which feedback loop is malfunctioning.

Figure 9:
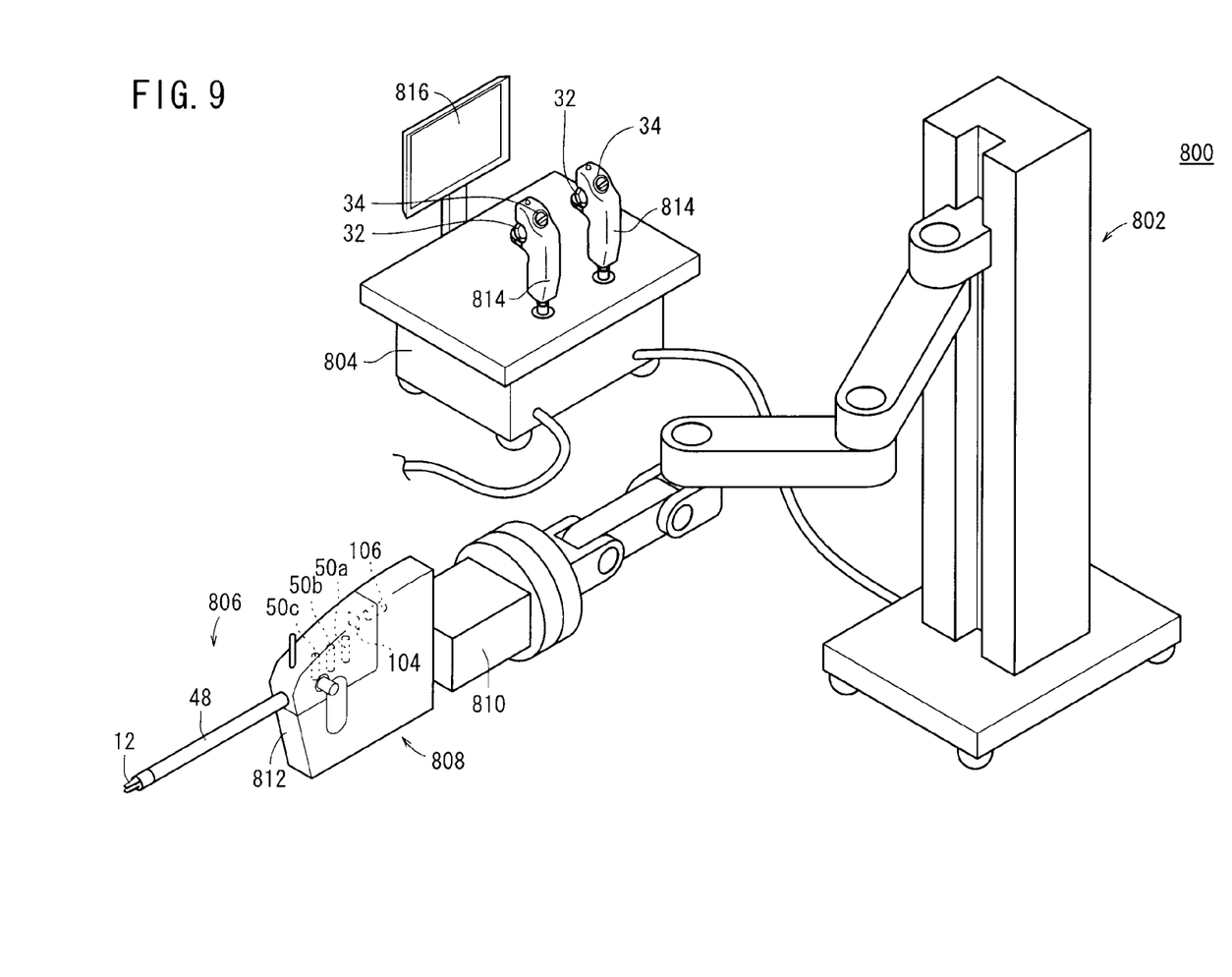
FIG. 9 is a schematic perspective view of a medical robot system with the manipulator connected to the distal end of a robot arm.

The medical manipulator 10 may be applied to a medical robot system 800 as shown in FIG. 9, for example.

The medical robot system 800 has an articulated robot arm 802 and a console 804, with a working unit 806 connected to a distal end of the robot arm 802. The distal end of the robot arm 802 incorporates therein a manipulator 808, which includes the same mechanisms as those of the medical manipulator 10. The manipulator 808 comprises the working unit 806. The robot arm 802 may comprise a means for moving the working unit 806, and is not limited to an installed type, but may be of an autonomous movable type. The console 804 may comprise a table type, a control panel type, or the like.

The robot arm 802 should preferably have six or more independent joints (rotary shafts, slide shafts, etc.) for setting the position and orientation of the working unit 806 as desired. The manipulator 808 is integrally combined with the distal end 810 of the robot arm 802. Instead of the actuator block 30 (see FIG. 1) described above, the manipulator 808 includes an actuator block 812, which is connected to the distal end 810 and incorporates motors therein.

The robot arm 802 operates under the control of the console 804, and may be automatically actuatable according to a program, by joysticks 814 mounted on the console 804, or by a combination of the program and the joysticks 814. The console 804 includes therein the aforementioned functions of the controller 27 (see FIG. 1). The working unit 806 includes the distal-end working unit 12, as described above.

The console 804 includes the two joysticks 814 serving as an operation command unit, and a monitor 816. Although not shown, the two joysticks 814 are capable of individually operating two robot arms 802. The two joysticks 814 are disposed in respective positions where the joysticks 814 can easily be operated by both hands of the operator. The monitor 816 displays information such as an image produced by an endoscope.

The joysticks 814 can be moved vertically and horizontally, or twisted and tilted, and the robot arm 802 can be moved depending on such movements of the joysticks 814. The joysticks 814 may be master arms. The robot arm 802 and the console 804 may communicate with other via a communication means comprising a wired link, a wireless link, a network, or a combination thereof.

Although a certain preferred embodiment of the present invention has been shown and described in detail, it should be understood that various changes and modifications may be made to the embodiment without departing from the scope of the invention as defined in the appended claims.

What is claimed is:

1. A medical manipulator comprising:
    an actuator block having a motor including a rotatable shaft;
    a coupler detachably mounted on the actuator block and having a rotor connected to the rotatable shaft of the motor;
    a distal-end working unit mounted on a distal end of a joint shaft, which extends from the coupler and is operatively connected to the rotor by a power transmitting member;
    an angle sensor for detecting an angular displacement of the motor; and
    a controller for reading a signal from the angle sensor and comparing the read signal with an operation command value for energizing the motor through a feedback loop,
    wherein the controller temporarily cuts off the feedback loop to turn the feedback loop into an open loop, outputs a current signal to the motor, and monitors the signal from the angle sensor within a range in which the distal-end working unit remains still, for thereby determining whether a system including the motor and the angle sensor is malfunctioning or not.

2. A medical manipulator according to claim 1, wherein the actuator block includes a speed reducer for reducing a speed of rotation of the motor and transmitting the rotation of the motor at the reduced speed to the rotor; and
    the controller determines whether the system is malfunctioning or not within a range in which an output shaft of the speed reducer remains still.

3. A medical manipulator according to claim 1, wherein the controller outputs signals to the motor to rotate the rotational shaft of the motor in respective normal and opposite directions.

4. A medical manipulator according to claim 1, wherein the controller determines whether the system is malfunctioning or not when the medical manipulator is initialized after the feedback loop is activated, and before the distal-end working unit is operated.

5. A medical manipulator comprising:
    an actuator block having a motor including a rotatable shaft;
    a coupler detachably mounted on the actuator block and having a rotor connected to the rotatable shaft of the motor;
    a distal-end working unit mounted on a distal end of a joint shaft, which extends from the coupler and is operatively connected to the rotor by a power transmitting member;
    an angle sensor for detecting an angular displacement of the motor; and
    a controller for reading a signal from the angle sensor and comparing the read signal with an operation command value for energizing the motor through a feedback loop,
    wherein the controller monitors the signal from the angle sensor within a range in which the distal-end working unit remains still, by outputting a signal having a level greater than the resolution of the angle sensor and a lower operation limit of the motor, for thereby determining whether a feedback system including the motor and the angle sensor is malfunctioning or not.

6. A medical manipulator comprising:
    an actuator block having a motor including a rotatable shaft;
    a coupler detachably mounted on the actuator block and having a rotor connected to the rotatable shaft of the motor;
    a distal-end working unit mounted on a distal end of a joint shaft, which extends from the coupler and is operatively connected to the rotor by a power transmitting member;
    an angle sensor for detecting an angular displacement of the motor;
    a controller for reading a signal from the angle sensor and comparing the read signal with an operation command value for energizing the motor through a feedback loop; and
    a current sensor for detecting a current value supplied to the motor and supplying the detected current value to the controller,
    wherein the controller inspects a system including the motor and the angle sensor for malfunctioning, when the signal from the angle sensor remains unchanged and the current value is equal to or greater than a threshold value, depending on an operation at a given time.

* * * * *